United States Patent
Oh

(10) Patent No.: US 11,566,227 B2
(45) Date of Patent: Jan. 31, 2023

(54) KIT CONTAINING MEDIUM FOR CULTURING NATURAL KILLER CELLS AND METHOD OF EFFECTIVELY CULTURING NATURAL KILLER CELLS USING THE SAME

(71) Applicant: FOREVERNK Inc., Seongnam-si (KR)

(72) Inventor: Jung Hoon Oh, Suwon-si (KR)

(73) Assignee: FOREVERNK INC., Seongnam-si (KR)

( * ) Notice: Subject to any disclaimer, the term of this patent is extended or adjusted under 35 U.S.C. 154(b) by 206 days.

(21) Appl. No.: 17/166,497

(22) Filed: Feb. 3, 2021

(65) Prior Publication Data

US 2021/0355445 A1 Nov. 18, 2021

(30) Foreign Application Priority Data

May 13, 2020 (KR) ........................ 10-2020-0056829

(51) Int. Cl.
*C12N 5/0783* (2010.01)
*C07K 16/28* (2006.01)

(52) U.S. Cl.
CPC .......... *C12N 5/0646* (2013.01); *C07K 16/283* (2013.01); *C07K 16/2809* (2013.01); *C12N 2500/32* (2013.01); *C12N 2501/2302* (2013.01); *C12N 2501/2312* (2013.01); *C12N 2501/2315* (2013.01); *C12N 2501/2317* (2013.01); *C12N 2501/2318* (2013.01)

(58) Field of Classification Search
None
See application file for complete search history.

(56) References Cited

FOREIGN PATENT DOCUMENTS

| KR | 10-1683614 B1 | 12/2016 |
|----|---------------|---------|
| KR | 10-1760764 B1 | 7/2017 |
| KR | 10-2018-0057359 A | 5/2018 |
| KR | 10-2087710 B1 | 3/2020 |

*Primary Examiner* — Zachary S Skelding
(74) *Attorney, Agent, or Firm* — Novick, Kim & Lee PLLC; Jae Youn Kim

(57) ABSTRACT

Disclosed is a method of culturing natural killer cells (NK cells) applied to immunotherapy. More specifically, disclosed are a kit containing a medium for culturing NK cells (NKCM kit) that can efficiently amplify and activate NK cells effective for the treatment of malignant tumors by culturing lymphocytes derived from human peripheral blood, and a method of culturing natural killer cells using the kit. The method for amplifying NK cells of the present invention includes stimulating NK cells with lymphocytes separated from peripheral blood, culturing the NK cells in a medium containing IL-2, IL-12, IL-15, IL-17, IL-18, and IL-21, and isolating the NK cells. Provided is a pharmaceutical composition for cell therapy containing NK cells produced by the method of amplifying NK cells. The pharmaceutical composition for cell therapy is expected to be widely used to treat infections and/or cancer.

2 Claims, 2 Drawing Sheets

KIT CONTAINING MEDIUM FOR CULTURING NATURAL KILLER CELLS AND METHOD OF EFFECTIVELY CULTURING NATURAL KILLER CELLS USING THE SAME

CROSS-RFERENCES TO RELATED APPLICATIONS

This application claims priority to and the benefit of Korean Patent Application No. 10-2020-0056829, filed on May 13, 2020, the disclosure of which is incorporated herein by reference in its entirety.

BACKGROUND OF THE INVENTION

Field of the Invention

The present invention relates to a method of culturing natural killer cells (NK cells) applied to immunotherapy, and more specifically, to a kit containing a medium for culturing NK cells that can efficiently amplify and activate NK cells, effective for treatment of malignant tumors, and can remarkably increase the proportion of NK cells by culturing lymphocytes derived from human peripheral blood and a method of culturing natural killer cells using the kit.

Description of the Related Art

Immunotherapy is a method that involves extracting the most important immune cells for cancer treatment, such as natural killer cells (NK cells), dendritic cells (DC), B cells, and T cells, from the blood of a patient and then growing immune cells capable of strongly defending against cancer using various types of stimulants and injecting the immune cells back into the patient. This method has been actively researched in recent years because it has few side effects due to the use of the patient's own blood and is administrated in a simple manner compared to conventional chemotherapy.

NK cells mainly attack cells having deteriorated or defective expression of MHC class I molecules while not attacking normal cells expressing the MHC class I molecules. Therefore, allogeneic NK cells have an advantage of preventing side effects of GVH (graft-versus-host) disease when used for cell therapy for cancer and infectious diseases. In fact, according to Miller et al. and Rubnitz et al., when NK cells were concentrated from fresh peripheral blood mononuclear cells derived from a cancer patient as a recipient and were then transplanted to a normal donor, which is an allied species (relative) of the recipient, the transplanted NK cells are engrafted temporarily and maintain cytotoxicity, without causing side effects on the recipient. However, there is no report on clinical therapy effective for NK cell transplantation. One reason therefor is that the number of cells that can be recovered by lymphocyte apheresis from a donor is limited, so NK cells cannot be retained in the body of the recipient in a number sufficient to kill target cells, such as cancer cells and pathogen-infected cells, until the target cells are killed.

Therefore, in order to retain NK cells in a number sufficient to kill target cells such as cancer cells and pathogen-infected cells in the body of the recipient until the target cells are killed, it is necessary to repeat several times transplantation of the NK cells, which is a great burden on the patient. Therefore, methods for obtaining NK cells in a number sufficient to kill target cells by culturing and amplifying NK cells obtained from donors in vitro have been developed.

Immune cells activated in immunotherapy, particularly NK cells, are large granular lymphocytes (LGL), a type of lymphocytes, which have excellent ability to kill infected viruses and tumor cells but do not kill most normal cells, and the anti-tumor action thereof is achieved through necrosis, apoptosis, or both of these mechanisms of action. NK cells respond to cytokines such as IL-2, IL-12, and interferon, thereby improving cytotoxicity, secretory and proliferative functions. The phenotypes of NK cells in humans are CD16 (FcγRIII) and CD56, and CD16 and CD56 do not have a T-cell receptor complex (TRC) on the cell surface, thus being used as markers for NK cells.

Such NK cells are known to play an important role in the early biodefense mechanisms and tumor immunity of the human body. In other words, NK cells can kill specific self-cells, allogeneic cells, and even xenogeneic cancer cells, and particularly can more effectively kill target cells that underexpress or do not express class 1 major histocompatibility complex (MHC-1), without the process of obtaining immunity by expression of the MHC. Thus, NK cells can effectively kill most cancer cells that do not express MHC, as well as several types of virus-infected cells and bacteria such as *Salmonella* typhi.

However, NK cells, which have potent activity of killing cancer cells, account for only 5 to 15% of peripheral blood lymphocytes even in normal humans, and in particular account for less than 1% of reduced peripheral blood lymphocytes in cancer patients. For this reason, ability to effectively attack cancer cells is limited without a separate amplification process through immunotherapy.

Cytokines such as IL-2 and antibodies such as anti-CD3 antibody are used to activate and proliferate immune cells, especially NK cells. With current technology, a CD3 antibody plays a pivotal role in the proliferation of immune cells. However, there is a problem in that it is difficult to activate immune cells using the CD3 antibody. In other words, the current conventional method for culturing immune cells mainly involves immobilizing a CD3 antibody in a flask and applying stimuli thereto for a certain period of time. However, there are differences in sensitivity to immune cells between respective subjects and great differences depending on the cell culture conditions or the skill level of the operators.

In particular, when strong stimulation is applied to the anti-CD3 antibody from the beginning, immature progenitor cells grow into T cells. For this reason, it is difficult to obtain activated NK cells that have been proliferated in a large amount using a generally used current method that involves initial slight stimulation of the CD3 antibody due to great difference depending on environmental factors such as individual differences.

In the current method, there is the need to develop a novel culture medium composition and a culture method that can be used to proliferate NK cells in large quantities by stably amplifying the NK cells while eliminating a cumbersome process of conducting a reaction for a certain period of time after immobilizing the CD3 antibody in the flask.

PRIOR ART

Patent Document (Patent Document 1) Korean Patent No. 10-2018-0057359
(Patent Document 2) Korean Patent Laid-Open No. 10-2087710

(Patent Document 3) Korean Patent Laid-Open No. 10-1683614
(Patent Document 4) Korean Patent Laid-Open No. 10-1760764

SUMMARY OF THE INVENTION

As a result of active research to solve the problems described above, the present inventors have developed a method that can stably amplify NK cells in a lymphocyte-conditioned medium without performing a process including immobilizing anti-CD3 antibodies, conducting a reaction for a certain period of time, and then removing the anti-CD3 antibodies. The present invention was completed based on this method.

Accordingly, it is one object of the present invention to provide a kit containing a medium for culturing NK cells having a composition that is capable of proliferating NK cells in large quantities through stable amplification in the finally obtained lymphocyte-conditioned medium, while eliminating a cumbersome process of culturing lymphocytes (immune cells) for a certain period of time in the state in which anti-CD3 antibodies are immobilized in a culture vessel in order to stimulate the lymphocytes.

It is another object of the present invention to provide a method of stably culturing NK cells having a low content of T cells and a high content of NK cells in the finally obtained lymphocyte-conditioned medium by sequentially using additives constituting a unit included in the kit containing the medium, that is, by setting a specific order of stimulation to the lymphocytes.

It is another object of the present invention to provide a kit containing a medium for culturing NK cells that is capable of extremely easily culturing NK cells by standardizing medium additives to be added in the culture step to proliferate NK cells at a remarkably high rate during lymphocyte culture, and a method of culturing NK cells using the same.

In accordance with the present invention, the above and other objects can be accomplished by the provision of a kit containing a medium for culturing NK cells including a basic solution containing L-glutamine, IL-2 and a medium for cell culture as a basic medium, a C-1 solution containing IL-12 in the basic solution, a C-2 solution containing IL-15 in the basic solution, a C-3 solution containing IL-17 and IL-21 in the basic solution, a C-4 solution containing IL-18 in the basic solution, an A-1 solution containing an anti-CD16 antibody and an anti-CD-56 antibody in the basic solution, and an A-2 solution containing an anti-CD3 antibody in the basic solution.

In addition, the basic solution of the present invention may contain the IL-2 at a concentration of 2,000 to 4,000 IU/mL, preferably 3,000 to 4,000 IU/mL.

In addition, the C-1 solution of the present invention may contain the IL-12 at a concentration of 0.5 to 5 ug/mL, preferably 0.5 to 3 ug/mL.

In addition, the C-2 solution of the present invention may contain the IL-15 at a concentration of 0.5 to 5 ug/mL, preferably 0.5 to 3 ug/mL.

In addition, the C-3 solution of the present invention may contain each of the IL-17 and the IL-21 at a concentration of 0.1 to 3 ug/mL, preferably 0.1 to 2 ug/mL.

In addition, the C-4 solution of the present invention may contain the IL-18 at a concentration of 0.5 to 5 ug/mL, preferably 0.5 to 3 ug/mL.

In addition, the A-1 solution of the present invention may contain each of the anti-CD16 antibody and the anti-CD56 antibody at a concentration of 0.1 to 20 ug/mL, preferably 0.5 to 5 ug/mL.

In addition, the A-2 solution of the present invention may contain the CD3 at a concentration of 0.1 to 20 ug/mL, preferably 0.5 to 5 ug/mL.

In accordance with another aspect of the present invention, provided is a method of culturing natural killer cells using the kit containing a medium for culturing cells according to the present invention, the method including a first step including adding a basic solution and an A-1 solution to separated lymphocytes and further adding autologous plasma thereto to stimulate NK cells, a second step of adding an A-2 solution and autologous plasma thereto to accelerate initial proliferation of the NK cells, a third step of adding C-1, C-2, C-3 and C-4 solutions and autologous plasma thereto to amplify culture of the NK cells, and a fourth step of amplifying and culturing the NK cells in the basic solution and the autologous plasma.

In addition, the autologous plasma of the present invention may be obtained when lymphocytes are separated from blood cells.

In addition, the autologous plasma of the present invention may be commercially available FBS or a substance similar thereto.

In addition, the autologous plasma of the present invention may be added in an amount of 10% v/v or less of the total medium.

In addition, the method may be characterized in that the number of immune cells is amplified by 100 to 500 times from the initial number of lymphocytes, which is 0.50 to $2.0 \times 10^7$, when the natural killer cells are cultured, and the proportion of killing-active cells including NK cells, NKT cells and gdT is 90% or more.

In accordance with another aspect of the present invention, provided is a method of preparing a pharmaceutical composition for treating an infection and/or cancer including the respective steps of the method of culturing natural killer cells described above.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
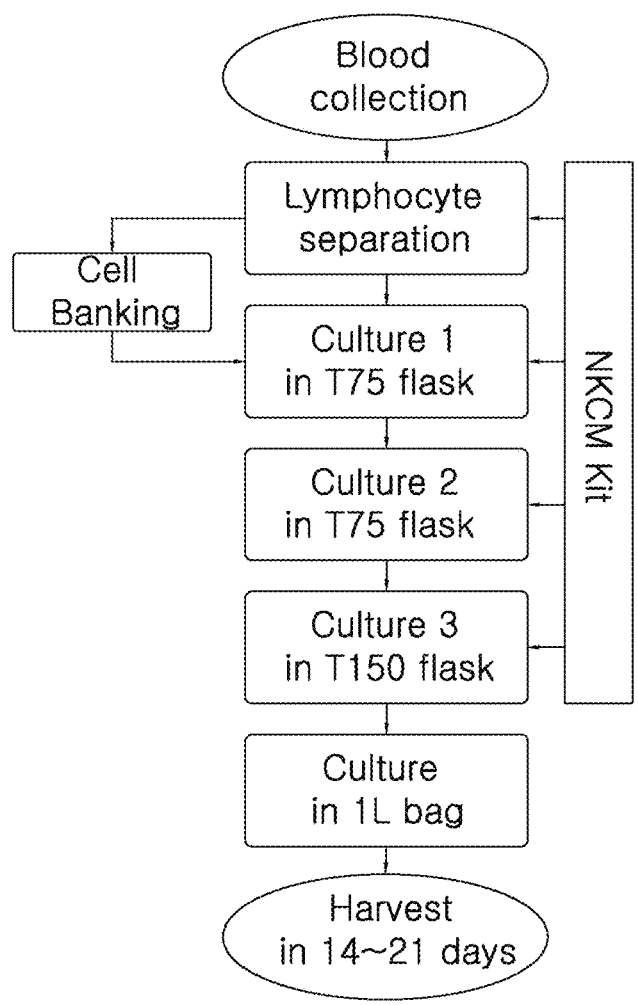
FIG. 1 is a diagram illustrating a culture protocol of a kit for culturing NK cells according to the present invention.

It will be understood that the terms used herein are used only to describe certain embodiments and should not be construed as limiting the scope of the present invention. Singular forms are intended to include plural forms as well, unless the context clearly indicates otherwise. It will be further understood that the term "comprises" or "has", when used in this specification, specify the presence of stated features, numbers, steps, operations, elements, components or combinations thereof, but does not preclude the presence or addition of one or more other features, numbers, steps, operations, elements, components, or combinations thereof.

It will be understood that the terms "first", "second", etc. may be used herein to describe various elements and should not be construed as limiting the elements. The terms are used only to distinguish one element from another element. For example, within the scope defined by the present invention, a "first" element may be referred to as a "second" element, and similarly, a "second" element may be referred to as a "first" element.

Unless differently defined herein, all terms used herein including technical or scientific terms have the same meanings as generally understood by those skilled in the art. In addition, terms identical to those defined in generally used dictionaries should be interpreted as having meanings identical to contextual meanings in the related art, and are not to be interpreted as having abnormal or excessively formal meanings unless they are definitely defined herein.

Hereinafter, the technical configuration of the present invention will be described in detail with reference to the attached drawings and preferred embodiments.

However, the present invention is not limited to the embodiments, and will be embodied in different forms. Like reference numbers refer to like elements throughout the description of the figures.

The technical feature of the present invention is directed to a kit containing a medium for culturing NK cells having a composition that is capable of proliferating NK cells in large quantities through stable amplification in the finally obtained lymphocyte-conditioned medium, without the cumbersome process of culturing lymphocytes (immune cells) for a certain period of time in the state in which anti-CD3 antibodies are immobilized in a culture vessel in order to stimulate the lymphocytes, and a method of culturing NK cells using the kit containing the medium.

In other words, in the present invention, by first performing stimulation using an anti-CD16 antibody and an anti-CD56 antibody and, after 24 hours, simply adding an anti-CD3 antibody to the medium, the number of NK cells can be stably increased from at least 500 times up to 5000 times.

As described above, the result of experimentation performed based on the principles developed in the present invention showed that, when immature progenitor cells are stimulated with an anti-CD16 antibody and an anti-CD56 antibody to induce differentiation of the progenitor cells into NK cells, mature NK cells are activated and T cells are stimulated with an anti-CD3 antibody to induce activation of the NK cells with the activated T cells, many NK cells were proliferated without any problem, even if stimulation was given, until the anti-CD3 antibody is degraded and removed in the culture medium. This proves that the culture method of the present invention is capable of culturing lymphocytes with a very high proportion of NK cells without the cumbersome process of culturing lymphocytes (immune cells) for a certain period of time in the state in which anti-CD3 antibodies are immobilized in a culture vessel in order to stimulate the lymphocytes.

EXAMPLE 1

Preparation of Culture Kit

A basic solution was prepared in a final amount of 10L by adding 2,000 to 4,000 IU/mL of IL-2 and 100 mL of a 500 mM L-glutamine solution to a basic medium for culturing suspending cells (when IL-2 or L-glutamine was already contained in the basic medium, the added amounts were changed to adjust the final concentration).

C-1 solution was prepared by dissolving IL-12 in the basic solution at a concentration of 0.5 to 3 ug/mL.

C-2 solution was prepared by dissolving IL-15 in the basic solution at a concentration of 0.5 to 3 ug/mL.

C-3 solution was prepared by dissolving each of IL-17 and IL-21 in the basic solution at a concentration of 0.1 to 2 ug/mL.

C-4 solution was prepared by dissolving IL-18 in the basic solution at a concentration of 0.5 to 3 ug/mL.

A-1 solution was prepared by dissolving each of an anti-CD16 antibody and an anti-CD56 antibody in the basic solution at a concentration of 0.5 to 5 ug/mL.

A-2 solution was prepared by dissolving an anti-CD3 antibody in the basic solution at a concentration of 0.5 to 5 ug/mL.

EXAMPLE 2

Proliferation and Culture of Natural Killer Cells Using Culture Kit

Lymphocytes and autologous plasma were prepared from the blood of patients and then natural killer cells were cultured using the kit containing a medium for culturing NK cells obtained in Example 1 as follows.

1. Lymphocyte Extraction and Autologous Plasma Preparation 30 ml of the peripheral blood of patient A was added to a 50 ml conical tube and centrifuged, and then the upper layer of autologous plasma was added to and treated with a heparin tube, and the result was added to a fresh 50 mL conical tube and was then centrifuged again to prepare the upper layer of plasma as autologous plasma.

Then, PBS was added to the blood tube from which the plasma has been removed to adjust the volume to 30 ml, thoroughly mixed, transferred to a tube containing Ficoll-Paque Plus, and centrifuged at 800 xg for 15 minutes, and a buffy coat layer containing lymphocytes, that is, the second layer, was separated and collected in a 50 mL conical tube, and the volume was adjusted to 50 mL with PBS, and then mixing was conducted. Then, centrifugation was performed 2 to 3 times, and then the supernatant was discarded and lymphocytes were separated.

2. Initial Culture

The basic solution, A-1 solution and autologous plasma were added to the separated lymphocytes, the result was incubated in a T25 or T75 flask in a $CO_2$ incubator (37° C., 5% $CO_2$) for 24 hours, and then A-2 solution was added thereto and incubated in the $CO_2$ incubator (37° C., 5% $CO_2$) for 48 hours (3 days in total).

3. Amplification Culture

After initial culture, C-1 solution, C-2 solution and autologous plasma were added to a T75 flask every 24 hours for 2 days, and C-1, C-2, C-3 and C-4 solutions and autologous plasma were further transferred to a T175 flask every 24 hours for 2 days and continuously incubated in a $CO_2$ incubator (37° C., 5% $CO_2$) (4 days in total).

4. Mass Culture

After amplification culture, the resulting entire culture solution was added to a 1L $CO_2$ permeable culture bag containing a cell culture medium, 5 to 10 mL of autologous plasma was further added thereto, massaged to be mixed thoroughly with the culture solution, and then incubated in a $CO_2$ incubator (37° C., 5% $CO_2$) for 4 to 6 days and massaged every 24 hours to be thoroughly mixed with the culture solution.

5. Harvesting of Natural Killer Immune Cells

The final culture solution obtained after culture was contained in a centrifuge tube, the cells were harvested through several rounds of centrifugation, and the harvested cells were packaged in a physiological saline bag and stored in a refrigerator or frozen.

Experimental Example 1 Immune Cell Proportion Analysis

Figure 2:
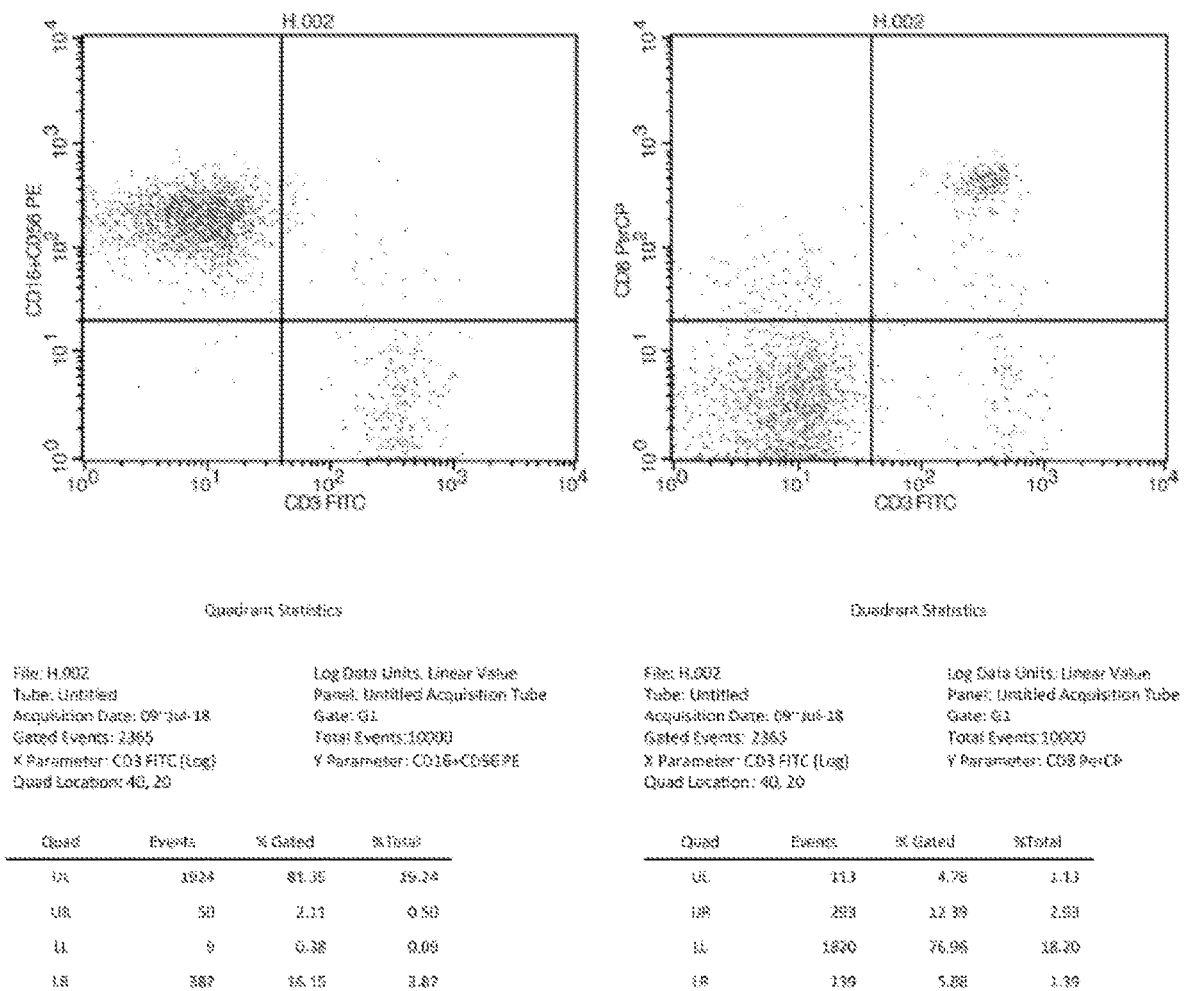
FIG. 2 is a diagram showing the phenotypic change of activated lymphocytes obtained according to an embodiment of the present invention.

The percentage of cells proliferated using the blood of patient A was analyzed. The result is shown in FIG. 2. As can be seen from FIG. 2, the percentage of NK cells is 81.35%, the percentage of NKT cells is 2.11%, and the percentage of gdT cells is 1.13%. This proves that about 92% or more of proliferated cells are killing-active cells that can exhibit therapeutic effects.

Experimental Example 2 Reproducibility of Immune Cell Culture in Subjects

An immune cell proliferation study was conducted using the above method, culture reproducibility was determined based on the following result of immune cell proliferation reproducibility, and the result is shown in Table 1 below.

TABLE 1

| Item | Harvested blood volume | Initial immune cell count | Total culture day | Final immune cell count |
| --- | --- | --- | --- | --- |
| Subject A | 60 mL | $0.53 \times 10^7$ | 14 days | $3.08 \times 10^9$ |
| Subject B | 60 mL | $1.44 \times 10^7$ | 14 days | $6.24 \times 10^9$ |
| Subject C | 60 mL | $1.82 \times 10^7$ | 14 days | $6.86 \times 10^9$ |
| Subject D | 60 mL | $0.88 \times 10^7$ | 14 days | $5.28 \times 10^9$ |

Experimental Example 3 Comparative Study with Other Culture Method

The culture method using IL-2, IL-12, IL-15, IL-17, IL-18, IL-21 and the anti-CD3 antibody, the anti-CD16 antibody and the anti-CD56 antibody (the kit of the present invention) was compared with other culture methods to determine the differentiation of the method using the kit of the present invention.

A. Comparative Study with Kit for Mass-Culturing Cells of KOHJIN BIO

The kit of the present invention was found to exhibit a higher immune cell count and a higher proportion of cells having killing activity when compared to culture using a known NK cell culture kit, specifically NK kit from KOHJIN BIO (NKCC-1, NKCC-2, NKCC-b, NKCC-c), for 14 days. The results are shown in Table 2 below.

TABLE 2

| Culture method | Target | Immune cell count before culture | Immune cell count after culture | NK cell proportion |
| --- | --- | --- | --- | --- |
| Kit of KOHJIN BIO | Health | $0.58 \times 10^7$ | $3.08 \times 10^9$ | 42% |
| | Patient | $0.42 \times 10^7$ | $1.71 \times 10^9$ | 33% |
| Kit of present invention | Health | $0.50 \times 10^7$ | $6.04 \times 10^9$ | 96% |
| | Patient | $0.38 \times 10^7$ | $4.27 \times 10^9$ | 88% |

B. Comparative Experiment Between Kit of Present Invention and Combination Culture Method The kit of the present invention was found to exhibit a higher immune cell count and a higher proportion of cells having killing activity when compared to a culture method of adding 2 0 a single culture solution containing a mixture of all of IL-2, IL-12, IL-15, IL-17, IL-18, IL-21, the anti-CD3 antibody, the anti-CD16 antibody, and the anti-CD56 antibody (Culture method A). The results are shown in Table 3 below.

TABLE 3

| Culture method | Target | Immune cell count before culture | Immune cell count after culture | NK cell proportion |
| --- | --- | --- | --- | --- |
| Culture method A | Health | $0.50 \times 10^7$ | $0.86 \times 10^9$ | 24% |
| | Patient | $0.36 \times 10^7$ | $0.45 \times 10^9$ | 27% |
| Kit of present invention | Health | $0.48 \times 10^7$ | $5.04 \times 10^9$ | 92% |
| | Patient | $0.38 \times 10^7$ | $4.42 \times 10^9$ | 89% |

C. Comparative Experiment Between Kit of Ppresent Invention and Culture Method Not Using Some Cytokines In order to compare the kit of the present invention with a culture method using the kit from which some cytokines are removed, a culture method, in which IL-17 and IL-21 are removed from the kit of the present invention (culture method B) was compared with the kit of the present invention. The kit of the present invention was found to exhibit a higher immune cell count and higher proportion of cells having killing activity when compared to the culture method B, and the results are shown in Table 4 below.

TABLE 4

| Culture method | Target | Immune cell count before culture | Immune cell count after culture | NK cell proportion |
| --- | --- | --- | --- | --- |
| Culture method B | Health | $0.55 \times 10^7$ | $1.74 \times 10^9$ | 42% |
| | Patient | $0.41 \times 10^7$ | $1.05 \times 10^9$ | 43% |
| kit of present invention | Health | $0.49 \times 10^7$ | $5.31 \times 10^9$ | 88% |
| | Patient | $0.33 \times 10^7$ | $4.22 \times 10^9$ | 85% |

As is apparent from the foregoing, the kit containing a medium for culturing NK cells according to the present invention has a composition that is capable of proliferating NK cells in large quantities through stable amplification in the finally obtained lymphocyte-conditioned medium, while eliminating the cumbersome process of culturing lymphocytes (immune cells) for a certain period of time in the state in which anti-CD3 antibodies are immobilized in a culture vessel in order to stimulate the lymphocytes.

The method of stably culturing NK cells is capable of providing activated lymphocytes having a low content of T cells and a high content of NK cells in the finally obtained lymphocyte-conditioned medium by sequentially using additives constituting a unit included in the kit containing the medium, that is, by setting a specific order of stimulation to the lymphocytes.

Although the preferred embodiments of the present invention have been disclosed, those skilled in the art will appreciate that various modifications, additions and substitutions are possible, without departing from the scope and spirit of the invention as disclosed in the accompanying claims.

The invention claimed is:

1. A method of culturing natural killer cells using a kit containing a medium for culturing cells comprising:
- a basic solution containing L-glutamine, IL-2 and a medium for cell culture;
- a C-1 solution containing IL-12 in the basic solution; a C-2 solution containing IL-15 in the basic solution;
- a C-3 solution containing IL-17 and IL-21 in the basic solution;
- a C-4 solution containing IL-18 in the basic solution;
- an A-1 solution containing an anti-CD16 antibody and an anti-CD-56 antibody in the basic solution;
- and an A-2 solution containing an anti-CD3 antibody in the basic solution, the method comprising:
- a first step comprising adding said basic solution and said A-1 solution to separated lymphocytes and further adding autologous plasma thereto to stimulate NK cells;
- a second step of adding said A-2 solution and autologous plasma thereto to accelerate initial proliferation of the NK cells;
- a third step of adding said C-1, C-2, C-3 and C-4 solutions and autologous plasma thereto to amplify culture of the NK cells;
- and a fourth step of amplifying and culturing the NK cells in the basic solution and the autologous plasma.

2. A method of preparing a pharmaceutical composition for treating an infection and cancer, the method comprising the respective steps of the method of culturing natural killer cells according to claim 1.

* * * * *